(12) United States Patent
Steiner et al.

(10) Patent No.: US 7,718,609 B2
(45) Date of Patent: *May 18, 2010

(54) RAPID ACTING AND LONG ACTING INSULIN COMBINATION FORMULATIONS

(75) Inventors: Solomon S. Steiner, Mount Kisco, NY (US); Roderike Pohl, Sherman, CT (US)

(73) Assignee: Biodel Inc., Danbury, CT (US)

( * ) Notice: Subject to any disclaimer, the term of this patent is extended or adjusted under 35 U.S.C. 154(b) by 141 days.

This patent is subject to a terminal disclaimer.

(21) Appl. No.: 11/734,161

(22) Filed: Apr. 11, 2007

(65) Prior Publication Data

US 2008/0039368 A1 Feb. 14, 2008

Related U.S. Application Data

(63) Continuation-in-part of application No. 11/695,562, filed on Apr. 2, 2007.

(60) Provisional application No. 60/744,687, filed on Apr. 12, 2006.

(51) Int. Cl.
A61K 38/28 (2006.01)
A61K 38/16 (2006.01)
A61K 31/185 (2006.01)
C07K 14/62 (2006.01)

(52) U.S. Cl. .............. 514/3; 514/2; 514/12; 530/300; 530/303; 530/324

(58) Field of Classification Search .............. None
See application file for complete search history.

(56) References Cited

U.S. PATENT DOCUMENTS

| | | |
|---|---|---|
| 2,143,590 A | 1/1939 | Scott |
| 2,626,228 A | 1/1953 | Petersen |
| 2,819,999 A | 1/1958 | Schlichtkrull |
| 3,649,456 A | 3/1972 | De Benneville et al. |
| 3,683,635 A | 8/1972 | Campanelli |
| 3,906,950 A | 9/1975 | Cocozza |
| 3,921,637 A | 11/1975 | Bennie, et al. |
| 4,129,560 A | 12/1978 | Zoltobrocki |
| 4,153,689 A | 5/1979 | Hirai |
| 4,196,196 A | 4/1980 | Tiholiz |
| 4,211,769 A | 7/1980 | Okada |
| 4,272,398 A | 6/1981 | Jaffe |
| 4,294,829 A | 10/1981 | Suzuki |
| 4,343,898 A | 8/1982 | Markussen |
| 4,377,482 A | 3/1983 | Rivier |
| 4,459,226 A | 7/1984 | Grimes |
| 4,489,159 A | 12/1984 | Markussen |
| 4,511,505 A | 4/1985 | Morihara |
| 4,659,696 A | 4/1987 | Hirai |
| 4,861,627 A | 8/1989 | Mathiowitz |
| 4,866,051 A | 9/1989 | Hunt |
| 4,946,828 A | 8/1990 | Markussen |
| 5,006,343 A | 4/1991 | Benson |
| 5,042,975 A | 8/1991 | Chien |
| 5,145,684 A | 9/1992 | Liversidge et al. |
| 5,188,837 A | 2/1993 | Domb |
| 5,204,108 A | 4/1993 | Illum |
| 5,260,306 A | 11/1993 | Boardman et al. |
| 5,352,461 A | 10/1994 | Feldstein |
| 5,354,562 A | 10/1994 | Platz |
| 5,364,838 A | 11/1994 | Rubsamen |
| 5,458,135 A | 10/1995 | Patton et al. |
| 5,474,978 A | 12/1995 | Bakaysa |
| 5,482,927 A | 1/1996 | Maniar |
| 5,484,606 A | 1/1996 | Dhabhar et al. |
| 5,492,112 A | 2/1996 | Mecikalski et al. |
| 5,503,852 A | 4/1996 | Steiner et al. |
| 5,514,646 A | 5/1996 | Chance et al. |
| 5,534,488 A | 7/1996 | Hoffmann |
| 5,547,929 A | 8/1996 | Anderson, Jr. et al. |
| 5,562,909 A | 10/1996 | Allcock et al. |
| 5,573,396 A | 11/1996 | Swanson |
| 5,577,497 A | 11/1996 | Mecikalski et al. |
| 5,650,486 A | 7/1997 | Felippis |

(Continued)

FOREIGN PATENT DOCUMENTS

| | | |
|---|---|---|
| CA | 2 136 704 | 5/1995 |
| DE | 247684 | 7/1987 |
| EP | 0/069/715 | 1/1983 |
| EP | 01/122/036 | 10/1984 |
| EP | 0 220 958 A2 | 5/1987 |

(Continued)

OTHER PUBLICATIONS

Human insulin, GenBank Accession No. AAA59172, pp. 1-2. Accessed Feb. 17, 2009.*

(Continued)

*Primary Examiner*—Anish Gupta
*Assistant Examiner*—Julie Ha
(74) *Attorney, Agent, or Firm*—Pabst Patent Group LLP

(57) ABSTRACT

A combined rapid acting-long acting insulin formulation has been developed in which the pH of the rapid acting insulin is adjusted so that the long acting glargine remains soluble when they are mixed together. In the preferred embodiment, this injectable basal bolus insulin is administered before breakfast, provides adequate bolus insulin levels to cover the meal, does not produce hypoglycemia after the meal and provides adequate basal insulin for 24 hours. Lunch and dinner can be covered by two bolus injections of a fast acting, or a rapid acting or a very rapid acting insulin. As a result, a patient using intensive insulin therapy should only inject three, rather than four, times a day.

15 Claims, 4 Drawing Sheets

U.S. PATENT DOCUMENTS

| | | | |
|---|---|---|---|
| 5,653,961 A | 8/1997 | McNally et al. |
| 5,653,987 A | 8/1997 | Modi et al. |
| 5,658,878 A | 8/1997 | Bäckström et al. |
| 5,672,359 A | 9/1997 | Digenis |
| 5,693,338 A | 12/1997 | Milstein |
| 5,740,794 A | 4/1998 | Smith et al. |
| 5,747,445 A | 5/1998 | Bäckström et al. |
| 5,763,396 A | 6/1998 | Weiner et al. |
| RE35,862 E | 7/1998 | Steiner et al. |
| 5,785,049 A | 7/1998 | Smith et al. |
| 5,785,989 A | 7/1998 | Stanley et al. |
| 5,807,315 A | 9/1998 | Van Antwerp et al. |
| 5,849,322 A | 12/1998 | Ebert et al. |
| 5,874,064 A | 2/1999 | Edwards et al. |
| 5,877,174 A | 3/1999 | Ono et al. |
| 5,888,477 A | 3/1999 | Gonda et al. |
| 5,898,028 A | 4/1999 | Jensen |
| 5,901,703 A | 5/1999 | Ohki et al. |
| 5,912,011 A | 6/1999 | Makino et al. |
| 5,929,027 A | 7/1999 | Takama et al. |
| 5,952,008 A | 9/1999 | Bäckström et al. |
| 5,976,569 A | 11/1999 | Milstein |
| 5,985,309 A | 11/1999 | Edwards et al. |
| 5,997,848 A | 12/1999 | Patton et al. |
| 6,051,256 A | 4/2000 | Platz et al. |
| 6,063,910 A | 5/2000 | Debenedetti |
| 6,071,497 A | 6/2000 | Steiner et al. |
| 6,099,517 A | 8/2000 | Daugherty |
| 6,132,766 A | 10/2000 | Sankaram et al. |
| 6,153,613 A | 11/2000 | Ono et al. |
| RE37,053 E | 2/2001 | Hanes et al. |
| 6,248,363 B1 * | 6/2001 | Patel et al. ................ 424/497 |
| 6,254,854 B1 | 7/2001 | Edwards et al. |
| 6,264,981 B1 | 7/2001 | Zhang |
| 6,294,204 B1 | 9/2001 | Rossling et al. |
| 6,310,038 B1 | 10/2001 | Havelund |
| 6,331,318 B1 | 12/2001 | Milstein |
| 6,395,744 B1 | 5/2002 | Adams et al. |
| 6,395,774 B1 | 5/2002 | Milstein |
| 6,423,344 B1 | 7/2002 | Platz et al. |
| 6,428,771 B1 | 8/2002 | Steiner et al. |
| 6,432,383 B1 | 8/2002 | Modi |
| 6,436,443 B2 | 8/2002 | Edwards et al. |
| 6,440,463 B1 | 8/2002 | Feldstein et al. |
| 6,444,226 B1 | 9/2002 | Steiner et al. |
| 6,447,753 B2 | 9/2002 | Edwards et al. |
| 6,465,425 B1 | 10/2002 | Tracy |
| 6,503,480 B1 | 1/2003 | Edwards et al. |
| 6,518,239 B1 | 2/2003 | Kuo et al. |
| 6,582,728 B1 | 6/2003 | Platz |
| 6,592,904 B2 | 7/2003 | Platz et al. |
| 6,635,283 B2 | 10/2003 | Edwards et al. |
| 6,652,885 B2 | 11/2003 | Steiner et al. |
| 6,676,931 B2 | 1/2004 | Dugger |
| 6,685,967 B1 | 2/2004 | Patton |
| 6,737,045 B2 | 5/2004 | Patton et al. |
| 6,949,258 B2 | 9/2005 | Zhang |
| 6,960,561 B2 | 11/2005 | Boderke |
| 7,030,084 B2 | 4/2006 | Ekwuribe et al. |
| 7,089,934 B2 | 8/2006 | Staniforth et al. |
| 7,192,919 B2 | 3/2007 | Tzannis |
| 7,279,457 B2 | 10/2007 | Pohl et al. |
| 2001/0039260 A1 | 11/2001 | Havelund |
| 2001/0043934 A1 | 11/2001 | L'Italien et al. |
| 2002/0198140 A1 | 12/2002 | Havelund |
| 2003/0017211 A1 | 1/2003 | Steiner |
| 2003/0064097 A1 | 4/2003 | Patel et al. |
| 2003/0068378 A1 | 4/2003 | Chen et al. |
| 2003/0172924 A1 | 9/2003 | Staniforth et al. |
| 2003/0194420 A1 | 10/2003 | Holl et al. |
| 2004/0077528 A1 | 4/2004 | Steiner |
| 2004/0096403 A1 | 5/2004 | Steiner |
| 2004/0151774 A1 | 8/2004 | Pauletti et al. |
| 2004/0157928 A1 | 8/2004 | Kim et al. |
| 2004/0182387 A1 | 9/2004 | Steiner |
| 2004/0247628 A1 | 12/2004 | Lintz et al. |
| 2005/0080000 A1 | 4/2005 | Thurow et al. |
| 2005/0153874 A1 | 7/2005 | Cheatham |
| 2005/0203001 A1 | 9/2005 | Arbit |
| 2005/0214251 A1 | 9/2005 | Pohl et al. |
| 2006/0067891 A1 | 3/2006 | Modi |
| 2007/0086952 A1 | 4/2007 | Steiner |
| 2007/0134279 A1 | 6/2007 | Stern |
| 2007/0155654 A1 | 7/2007 | Langkjaer |
| 2007/0235365 A1 | 10/2007 | Pohl et al. |
| 2008/0039365 A1 | 2/2008 | Steiner et al. |
| 2008/0085298 A1 | 4/2008 | Pohl et al. |
| 2008/0090753 A1 | 4/2008 | Pohl et al. |
| 2008/0096800 A1 | 4/2008 | Pohl et al. |

FOREIGN PATENT DOCUMENTS

| | | |
|---|---|---|
| EP | 0/237/507 | 9/1987 |
| EP | 0 257 915 | 2/1988 |
| EP | 0/360/340 | 3/1990 |
| EP | 0/364/235 | 4/1990 |
| EP | 0/606/486 | 12/1993 |
| EP | 0748213 | 12/1996 |
| EP | 1/114/644 | 7/2001 |
| EP | 1 428 524 | 6/2004 |
| GB | 2 069 502 | 8/1981 |
| GB | 2240337 | 7/1991 |
| JP | 0149545 | 2/1992 |
| JP | 363020301 A | 1/1998 |
| WO | WO 90/13285 | 11/1990 |
| WO | WO 91/04011 | 4/1991 |
| WO | WO 91/08764 | 6/1991 |
| WO | WO 91/16882 | 11/1991 |
| WO | WO 92/04069 | 3/1992 |
| WO | WO 92/08509 | 5/1992 |
| WO | WO 93/02712 | 2/1993 |
| WO | WO 93/17728 | 9/1993 |
| WO | WO 93/18754 | 9/1993 |
| WO | WO 94/00291 | 1/1994 |
| WO | WO 95/00127 | 1/1995 |
| WO | WO 95/11666 | 5/1995 |
| WO | WO 95/31979 | 11/1995 |
| WO | WO 95/34294 | 12/1995 |
| WO | WO 96/10996 | 4/1996 |
| WO | WO 96/36314 | 11/1996 |
| WO | WO 96/36352 | 11/1996 |
| WO | WO 97/33531 | 9/1997 |
| WO | WO 97/49386 | 12/1997 |
| WO | WO 98/42367 | 10/1998 |
| WO | WO 98/42368 | 10/1998 |
| WO | WO 98/42749 | 10/1998 |
| WO | WO 99/52506 | 10/1999 |
| WO | WO 01/00654 | 1/2001 |
| WO | WO 01/07107 | 2/2001 |
| WO | WO 02/11676 | 2/2002 |
| WO | WO 03/057170 | 7/2003 |
| WO | WO 03/086345 | 10/2003 |
| WO | WO 03/094951 | 11/2003 |
| WO | WO 03/101395 | 12/2003 |
| WO | WO 2004/056314 | 7/2004 |
| WO | WO 2004/075919 | 9/2004 |
| WO | WO 2004/080401 | 9/2004 |
| WO | WO 2005/089722 | 9/2005 |
| WO | WO 2006/088473 | 8/2006 |
| WO | WO 2007/041481 | 4/2007 |
| WO | WO 2007/047948 | 4/2007 |

WO WO 2007/121256 10/2007

OTHER PUBLICATIONS

Bovine insulin, GenBank Accession No. ACD35246, pp. 1-2. Accessed Feb. 17, 2009.*
Types of Insulin from http://www.diabetes.org/for-parents-and-kids/diabetes-care/types-action.jsp, pp. 1-2. Accessed Feb. 17, 2009.*
Lantus (Medical News Today) from http://www.medicalnewstoday.com/articles/127409.php, pp. 1-6. Accessed Jun. 18, 2009.*
The Aventis Pharmaceutical Lantus Prescribing Information from http://products.sanofi-aventis.us/lantus/lantus.html, pp. 1-45. Accessed Apr. 30, 2009.*
Novo Nordisk from www.novonordisk-us.com, pp. 1-15. Accessed Apr. 30, 2009.*
Diabetes Forecast from 2008 Resource Guide, RG11-RG-14. 2008.*
Lalli C, Ciofetta M, Del Sinaco P, Torlone E, Pampanelli S, Compagnucci P, Giulia M, Bartocci L, Brunetti P, Bolli GB, "Long-term intensive treatment of type 1 Diabetes with the Short-Acting insulin analog Lispro in variable combination with NPH insulin at mealtime," Diabetes Care, 1999, 22(3): 468-477.*
Molitch ME, "How long should insulin be used once a vial is started?" from Diabetes Care, 2004, 27(5): 1240-1242.*
Roach P, Yue L, Arora V, "Improved Postprandial Glycemic Control During Treatment With Humalog Mix 25, a Novel Protamine-Based Insulin Lispro Formulation," Diabetes Case, 1999, 22(8): 1258-1261.*
Culy CR, Jarvis B, "Management of Diabetes Mellitus: Defining the Role of Insulin Lispro Mix 75/25," Drugs in Disease Management, 2001, 9(12): 711-730.*
HUMULOG® Mix75/25TM product sheet from Eli Lilly, PV 5580AMP, pp. 1-4. Accessed Jun. 18, 2009.*
Edelman, et al., "A double-blinded placebo-controlled trial assessing pramlintide treatment in the setting of intensive insulin therapy in type 1 diabetes", Diabetes Care, 29(10):2189-2195 (2006).
Nilsson, et al., "Low levels of asparagine deamidation can have a dramatic effect on aggregation of amyloidogenic peptides: implications for the study of amyloid formation", Protein Science, 11(2): 342-349 (2002).
U.S. Appl. No. 12/324,717, filed Nov. 28, 2008, Steiner, et al.
Davidson, et al.," Effect of premixed nph and regular insulin on glucose control and health-related quality of life in patients with type 2 diabetes mellitus", Endocrine Practice, 3(6):331-336 (1997).
Aungst & Rogers, "Site dependence of absorption-promoting actions of laureth-9, Na salicylate, Na2EDTA, and aprotinin on rectal, nasal, and buccal insulin delivery", Pharm. Res., 5(5):305-308 (1988).
Brange, et al., Chemical stability of insulin 1: hydrolytic degradation during storage of pharmaceutical preparations, Pharm. Res., 9:715-726 (1992).
De Sousa, et al., "Biocompatibility of EDTA, EGTA and citric acid", Braz. Dent. J., 16:3-8 (2005).
Kang, et al., "Subcutaneous insulin absorption explained by insulin's physiochemical properties", Diabetes Care, 14:942-948 (1991).
Keowmaneechai, et al, "Influence of EDTA and citrate on physiochemical properties of whey protein-stabilized oil-in-water emulsions containing $CaCl_2$", J. Agricultural and Food, Chemistry, 50:7145-7153 (2002).
Klauser, et al., "Mixtures of human intermediate and human regular insulin in type 1 diabetic patients", Diabetes Res. and Clin. Practice, 5:185-190 (1988).
Monch & Dehnen, "High-performance liquid chromatography of polypeptides and proteins on a reversed-phase support", Journal of Chromatography,147:415-418 (1978).
Quinn, et al., "Minimizing the aggregation of insulin solutions", J. Pharmaceutical Sci., 72:1472-1473 (1983).
Szepesy & Horvath, "Specific salt effects in hydrophobic interaction chromatography of proteins", Chromatographia, 26:13-18 (1988).
Todo, et al., "Effect of additives on insulin absorption from intracheally administered dry powders in rats", Int. J. Pharmaceutics, 220:101-110 (2001).
Bauer, et al.,"Assessment of beta-adrenergic receptor blockade after isamoltane, a 5-HT1-receptor active compound, in healthy volunteers," Clin. Pharmacol Ther 53:76-83 (1993).

Benita, "Characterization of Drug-Loaded Poly(d,l-lactide) Microspheres," J. Pharm. Sci.,73: 1721-1724 (1984).
Bensch, et al., "Absorption of intact protein molecules across the pulmonary air-tissue barrier," Science 156: 1204-1206 (1967).
Brange, et al., "Insulin Structure and stability", Pharm Biotechnol., 5:315-50 (1993).
Cerasi, et al., "Decreased sensitivity of the pancreatic beta cells to glucose in prediabetic and diabetic subjects. A glucose dose-response study," Diabetes 21(4): 224-34 (1972).
Cefalu, et al, "Inhaled Human Insulin Treatment in Patients with type 2 diabetes mellitus," Ann. Int. Med., 134: 203-7 (2001).
Cheatham and Pfeutzner, "Desirable dynamics & performance of inhaled insulin compared to subcutaneous insulin given at mealtime in type 2 diabetes: A report from the technosphere/insulin study group" Diabetes Technology & Therapeutics 6:234-235 (2004).
Costello, et al., "Zinc inhibition of mitochondrial aconitase and its importance in citrate metabolism in prostate epithelial cells", Journ. Biol. Chem., 272(46):28875-28881 (1997).
Dieter Köhler, "Aerosols for Systemic Treatment", Lung (Suppl), 677-684 (1990).
Dunn, "Zinc-ligand interactions modulate assembly and stability of the insulin hexamer", Biometals, 18(4):295-303 (2005).
Edelman, "Type II Diabetes Mellitus," Advances in Internal Medicine, 43:449-500 (1998).(Abstract).
Elliott, et al., "Parenteral absorption of insulin from the lung in diabetic children," Austr. Paediatr. J. 23: 293-297 (1987).
Engelgau, et al., "Screening for tyoe 2 diabetes," Diabetes Care 1563(23):1-31 (2000).
Festa, et al., "LDL particle size in relation to insulin, proinsulin, and insulin sensitivity" Diabetes Care 22(10):1688-1693 (1999).
Garber, "Premixed insulin analogues for the treatment of diabetes mellitus", Drugs, 66(1):31-49 (2006).
Gupta, "Contemporary Approaches in Aerosolized Drug Delivery to the Lung," J. Controlled Release, 17(2): 127-147 (1991).
Haffner, et al., "Proinsulin and insulin concentrations I relation to carotid wall thickness" Stroke 29:1498-1503 (1998).
Hagedorn, et al., "Protamine insulin", JAMA, 106:177-180 (1936).
Hanley et al., "Cross-sectional and prospective associations between proinsulin and cardiovascular disease risk factors in a population experiencing rapid cultural transition" Diabetes Care 24(7):1240-1247 (2001).
Heubner, et al. Klinische Wochenschrift 16,2342 (1924).
Heyder, "Alveolar deposition of inhaled particles in humans," Am. Ind. Hyg. Assoc. J. 43(11): 864-866 (1982).
Heyder, "Particle Transport onto Human Airway Surfaces" Eur. J. Respir. Dis. Suppl. 119, 29-50 (1982).
Johnson, et al, "Turbuhaler®: a new device for dry powder terbutaline inhalation," Allergy 43(5):392-395 (1988).
Jones, et al., "An investigation of the pulmonary absorption of insulin in the rat", Third European Congress of Biopharmaceutics and Pharmacokinetics, 1987.
Katchalski, "Synthesis of Lysine Anhydride," J. Amer. Chem. Soc., 68: 879-880 (1946).
Kohler, et al., "Pulmonary Administration . . . ," Abstract 298, Diabetes 33 (Suppl.):75A (1984).
Kohler, "Aerosols for Systemic Treatment", Lung Suppl. 677-683 (1990).
Komada, et al., "Intratracheal delivery of peptide and protein agents: absorption from solution and dry powder by rat lung," J. Pharm. Sci. 83(6): 863-867 (1994).
Kontny, et al."Issues Surrounding MDI Formulation Development with Non-CFC Propellants," J. Aerosol Med. 4(3), 181-187 (1991).
Kopple, "A Convenient Synthesis of 2,5-Piperazinediones," J. Org. Chem., 33(2): 862-864 (1968).
Leahy, "Beta-cell dysfunction in type II diabetes mellitus," Curr. Opin. Endocrinol. Diabetes 2(4): 300-306 (1995).
Lee, et al., "Development of an Aerosol Dosage Form Containing Insulin," J. Pharm. Sci. 65(4), 567-572 (1976).
Lian, et al., "A self-complementary, self-assembling microsphere system: application for intravenous delivery of the antiepileptic and neuroprotectant compound felbamate," J Pharm Sci 89:867-875 (2000).

Lim, "Microencapsulation of Living Cells and Tissues," *J. Pharm. Sci.*, 70: 351-354 (1981).

Mathiowitz, "Morphology of Polyanhydride Microsphere Delivery Systems," *Scanning Microscopy*, 4: 329-340 (1990).

Mathiowitz, "Novel Microcapsules for Delivery Systems," *Reactive Polymers*, 6: 275-283 (1987).

Mathiowitz, "Polyanhydride Microspheres As Drug Carriers I. Hot-Melt Microencapsulation," *J. Controlled Release*, 5: 13-22 (1987).

Mathiowitz, "Polyanhydride Microspheres As Drug Carriers II. Microencapsulation by Solvent Removal," *J. Applied Poly. Sci.*, 35: 755-774 (1988).

Mathiowitz, "Polyanhydride Microspheres IV. Morpohology and Characterization of Systems Made by Spray Drying," *J. Applied Poly. Sci.*, 45: 125-134 (1992).

Nagai, et al., "Powder Dosage Form of Insulin for Nasal Administration," *J. Control Rel.*,1:15-22 (1984).

Okumura, et al., "Intratracheal delivery of insulin. Absorption from solution and aerosol by rat lung," *Int. J. Pharmaceuticals* 88: 63-73 (1992).

Patton & Platz, "Routes of Delivery: Case Studies. Pulmonary delivery of peptides and proteins for systemic action," *Adv. Drug. Del. Rev.* 8: 179-196 (1992).

Pfeiffer, "Insulin secretion in diabetes mellitus," *Am. J. Med.* 70(3): 579-88 (1981).

Pfutzner, et al., "Influence of small dose i.v., s.c. and pulmonary insulin treatment on prandial glucose control in patients with type 2 diabetes" *37th Annual Meeting of the EASD, Glasgow*, Sep. 9-13, 2001 812 (2001) (abstract).

Polonsky, et al., "Abnormal patterns of insulin secretion in non-insulin-dependent diabetes mellitus," *N. England J. Med.* 318(19): 1231-39 (1988).

Prabhu, et al. "A study of factors controlling dissolution kinetic of zinc complexed protein suspensions in various ionic species", *Int. J. Pharm.*, 217(1-2):71-8 (2001).

Raskin, et al., "Continuous subcutaneous insulin infusion and multiple daily injection therapy are equally effective in type 2 diabetes" *Diabetes Care* 26:2598-2603 (2003).

Rosenstock, et al., "Reduced hypoglycemia risk with insulin glargine: a meta-analysis comparing insulin glargine with human NPH insulin in type 2 diabetes", Diabetes Care, 28(4):950-5 (2005).

Sakr, "A new approach for insulin delivery via the pulmonary route: design and pharmacokinetics in non-diabetic rabbits", *International Journal of Pharmaceutics*, 86:1-7 (1992).

Salib, "Utilization of Sodium Alginate in Drug Microencapsulation," *Pharazeutische Industrie* , 40(11a): 1230-1234 (1978).

Sawhney, "Bioerodible Hydrogels Based on Photopolymerized Poly-(ethylene glycol)-co-poly(a-hydroxy acid) Diacrylate Macromers," *Macromolecules*, 26: 581-587 (1993).

Schluter, et al., "Pulmonary Administration of Human Insulin in Volunteers and Type I Diabetics", *Diabetes*, 33 (Suppl.): 298 (1984).

Schneider, et al., "Stimulation by proinsulin of expression of plasminogen activator inhibitor type-I in endothelial cells" *Diabetes* 41(7):890-895 (1992).

Warren, et al., "Postprandial versus preprandial dosing of biphasic insulin aspart in elderly type 2 diabetes patients" *Diabetes Research and Clinical Practive* 66:23-29 (2004).

Waterhouse, et al. "Comparative assessment of a new breath-actuated inhaler in patients with reversible airways obstruction." *Respiration* 59:155-158 (1992).

Wigley, et al., "Insulin across respiratory mucosae by aerosol delivery," *Diabetes* 20(8): 552-556 (1971).

Witchert, "Low Molecular Weight PLA: A Suitable Polymer for Pulmonary Administered Microparticles," *J. Microencapsulation*, 10(2): 195-207 (1993).

Yoshida, et al., "Absorption of insulin delivered to rabbit trachea using aerosol dosage form," *J. Pharm. Sci.* 68(5): 670-671 (1979).

Zethelius, et al., "Proinsulin is an Independent Predictor of Coronary Heart Disease" *Circulation* 105:2153-2158 (2002).

U.S. Appl. No. 12/348,839, filed Jan. 5, 2009, Kashyap, et al.

Actrapid, "Summary of product characteristics", http://emc.medicines.org.uk/medicine/3513/SPC/Actrapid+100+IU+ml,+Solution+for+Injection+in+a+vial/, pp. 1-6; revised (2007); (accessed Apr. 20, 2009).

Kashyap, "Design and evaluation of biodegradable, biosensitive in situ gelling system for pulsatile delivery of insulin" *Biomaterials*, 28(11):2051-60 (2007). Epub Jan. 19, 2007.

Talrose, et al., "Radiation resistivity of frozen insulin solutions and suspensions", *Int J. Appl. Radiat. Isot.*, 32(10):753-6 (1981).

Traitel, et al., "Characterization of glucose-sensitive insulin release systems in simulated in vivo conditions", *Biomaterials*, 21(16):1679-87 (2000).

Velosulin, "Information for health professionals, Production Data Sheet", http://www.medsafe.govt.nz/profs/datasheet/v/VelosulinMCinj.htm, pp. 1-5; (2000); (accessed Apr. 20, 2009).

Zhang, et al., "Modulated insulin permeation across a glucose-sensitive polymeric composite membrane", *J. Control Release*, 80(1-3):169-78 (2002).

U.S. Appl. No. 12/397,219, filed Mar. 3, 2009, Steiner, et al.

Berge, et al. "Pharmacuetical Salts," *J. Pharmaceutical Sciences* 66(1):1-19 (1977).

Heinemann, et al. "Current Status of the development of inhaled insulin" *Br. J. Diabetes Vasc Dis* 4:295-301 (2004).

Karl, et al., Pramlintide as an adjunct to insulin in patients with type 2 diabetes in a clinical practice setting reduced AIC, postprandial glucose excursions, and weight, *Diabetes Technology And Therapeutics*, 9(2):191-199 (2007).

Kohler, et al. "Non-radioactive approach for measuring lung permeability: inhalation of insulin," *Atemw Lungebkrkh* 13:230-232 (1987).

Moren, "Aerosol dosage forms and formulations" in *Aerosols in Medicine*, (2nd ed.), Elsevier, pp. 321-350 (1993).

Plum, et al., "Pharmacokinetics of the rapid-acting insulin analog, insulin aspart, in rats, dogs, and pigs, and pharmacodynamics of insulin aspart in pigs.", *Drug Metab. Dispos.*, 28(2):155-60 (2000).

Raz, et al. "Pharmacodynamic and pharmacokinetics of dose ranging effects of oralin versus s.c. regular insulin in Type 1 diabetic patients," *Fourth Annual Diabetes Technology Meeting*, Philadelphia, PA, 2004.

Steiner, et al. "Technosphere ™/ Insulin- proof of concept study with new insulin formulation for pulmonary delivery" *Exp. Clin. Endocrinol. Diabetes* 110:17-21 (2002).

US 5,785,981, 07/1998, Stanley et al. (withdrawn)

* cited by examiner

RAPID ACTING AND LONG ACTING INSULIN COMBINATION FORMULATIONS

CROSS-REFERENCE TO RELATED APPLICATIONS

This application is a continuation-in-part of U.S. Ser. No. 11/695,562 filed Apr. 2, 2007, by Solomon S. Steiner and Roderike Pohl, which claims priority to U.S. Ser. No. 60/744,687 entitled "Rapid Acting and Long Acting Insulin Combination Formulations" filed Apr. 12, 2006 by Solomon S. Steiner and Roderike Pohl and U.S. Ser. No. 11/537,335 entitled "Rapid Acting and Prolonged Acting Insulin Preparations" filed Sep. 29, 2006 by Solomon S. Steiner and Roderike Pohl.

BACKGROUND OF THE INVENTION

The present invention generally relates to formulations combining rapid acting and long acting insulin formulations.

Intensive insulin therapy for diabetes involves providing a basal insulin, ideally present at a uniform level in the blood over a 24 hour period and a bolus or meal time (prandial) insulin to cover the added carbohydrate load from digestion concomitant with each meal.

In 1936, Hans Christian Hagedorn and B. Norman Jensen discovered that the effects of injected insulin could be prolonged by the addition of protamine obtained from the "milt" or semen of river trout. The insulin was added to the protamine and the solution was brought to pH 7 for injection. In 1946, Nordisk Company was able to form crystals of protamine and insulin and marketed it in 1950 as NPH, (Neutral Protamine Hagedorn, "NPH") insulin. NPH insulin has the advantage that it can be mixed with an insulin that has a faster onset to compliment its longer lasting action. Eventually all animal insulins were replaced by human recombinant insulin.

Until very recently, and in many places today, basal insulin is usually provided by the administration of two daily doses of NPH insulin, separated by 12 hours. A patient eating three meals a day and using NPH insulin as the basal insulin requires five injections per day, one with each of three meals and two NPH insulin injections, one in the morning and the other at bedtime. To reduce the number of injections the patient must take, the morning dose of NPH insulin has been combined with a short acting insulin, (recombinant human insulin) or a rapid acting insulin analog, such as lispro. A typical combination is a 70% NPH to 30% rapid acting insulin analog mixture. As a result, the patient can reduce the number of injections from five per day to four per day. See, for example, Garber, Drugs 66(1):31-49 (2006).

More recently insulin glargine, (trade name LANTUS®) a "very long-acting" insulin analog has become available. It starts to lower blood glucose about one hour after injection and keeps working evenly for 24 hours. J. Rosenstock and colleagues found that patients who took insulin glargine had a much lower risk of low blood glucose (hypoglycemia) than the patients who took NPH insulin.

Glargine cannot be mixed with other short or rapid acting insulins because the mixture causes glargine to precipitate prior to injection and administration of a precipitated insulin makes it virtually impossible to administer a known and reliable dose. The manufacturer of glargine warns users against mixing glargine with any other insulin.

It is therefore an object of the present invention to provide insulin formulations that can be used to reduce the number of daily injections to three.

It is another object of the present invention to provide a basal-bolus insulin formulation.

It is still another object of the present invention to provide a stable insulin formulation having immediate and long term release characteristics.

SUMMARY OF THE INVENTION

A combined fast or rapid acting-long acting insulin formulation has been developed wherein the pH of the fast or rapid acting insulin is adjusted so that both rapid and long acting insulins remain soluble when they are mixed together. Included in the preferred embodiment are any very rapid, rapid or fast acting insulin formulations combined with any intermediate, long or very long acting insulin at low pH. In another embodiment, any very rapid, rapid, or fast insulin can be combined with any intermediate, long or very long acting insulin at low pH, in the presence of a chelating agent. In the most preferred embodiment, VIAJECT™ (a very rapid acting insulin) is mixed with insulin glargine at pH4 to produce a rapid initial spike in blood insulin concentration to cover the carbohydrates being absorbed from digestion of a meal and continue with a sustained basal blood insulin concentration.

When an injectable basal bolus insulin formulation is co-administered with a rapid or very rapid acting insulin before breakfast, it provides adequate bolus insulin levels to cover the meal, does not produce hypoglycemia after the meal and provides adequate basal insulin for 24 hours. Lunch and dinner can be covered by two bolus injections of a fast acting, or a rapid acting or a very rapid acting insulin. As a result, a patient using intensive insulin therapy would only inject three, rather than four, times a day.

Experiments have been performed to demonstrate the importance of the addition of specific acids such as aspartic acid, glutamic acid, maleic, fumaric, or succinic acid to hexameric insulin to enhance speed and amount of absorption and preserve bioactivity following dissociation into the dimeric/monomeric form. These are added in addition to a chelator, preferably ethylenediaminetetraacetic acid (EDTA). Polyacids were selected based on their molecular size and structure to optimize association with hydrogen bonding sites on the insulin surface, effectively masking charged amino acid residues FIG. 1, regardless of the source (including native insulin, recombinant insulin, long acting insulin, porcine, bovine, insulin derivatives and analogues thereof). The acids were used at a concentration that provided optimal charge masking effect, (As shown by the examples, the preferred acids are aspartic, glutamic, succinic, maleic, fumaric and citric acid) The combination of both the preferred acid and the chelator together in the insulin formulation appear to be responsible for rapid insulin absorption. EDTA was not effective with all acids. When used with adipic acid, oxalic acid or HCl, there was no apparent increase in the rate of absorption of insulin. These studies establish the importance of an acid and chelator in both in vitro (human oral epithelial cells) and in vivo (rat, pig and human) studies. These findings confirm the results seen in patients with diabetes treated with the very rapid acting insulin (in combination with citric acid and EDTA) and the basal insulin glargine.

DETAILED DESCRIPTION OF THE INVENTION

I. Compositions

A. Insulin

Figure 1:
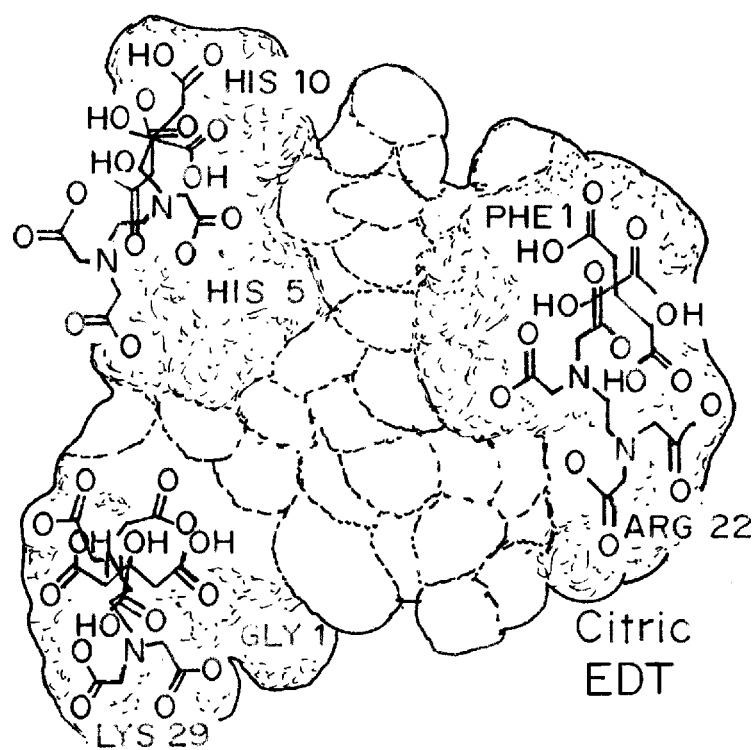
FIG. 1 is a three dimensional schematic of insulin showing charges.

The composition includes a fast, rapid or very rapid acting insulin and an intermediate or long acting insulin. The rapid acting insulin is provided at a low pH, at which the long acting insulin does not precipitate when mixed together, even over a wide range of ratios of rapid acting to long acting insulin.

There are several differing types of commercial insulin available for diabetes patients. These types of insulins vary according to (1) how long they take to reach the bloodstream and start reducing blood glucose levels; (2) how long the insulin operates at maximum strength; and (3) how long the insulin continues to have an effect on blood sugar.

Fast Acting Insulin

Fast acting insulins are intended to respond to the glucose derived from ingestion of carbohydrates during a meal. Fast acting insulins start to work within one to 20 minutes, peaking about one hour later and lasting from three to five hours. Fast acting insulin takes about two hours to fully absorb into the systemic circulation. Fast acting insulins include regular recombinant human insulin (such as HUMULIN®, marketed by Lilly, and NOVOLIN®, marketed by NovoNordisk) which are administered in an isotonic solution at pH 7. Bovine and porcine insulins, which differ in several amino acids to human insulin, but are bioactive in humans, are also fast acting insulins.

Rapid Acting Insulin.

Some diabetes patients use rapid-acting insulin at mealtimes, and long-acting insulin for 'background' continuous insulin. This group include insulins that have been modified or have altered locations of amino acids in order to enhance their rate of absorption.

At present there are three types of rapid-acting commercial insulin analogs available: lispro insulin (Lysine-Proline insulin, sold by Eli Lilly as HUMALOG®), glulisine insulin (sold by Sanofi-Aventis as APIDRA®) and aspart insulin (sold by Novo Nordisk as NOVOLOG®).

Very Rapid Acting Insulin

Biodel has a proprietary insulin formulation of regular human insulin that is even more rapid than the rapid acting insulin analogs, VIAJECT™. This is a formulation combining regular human insulin with EDTA and citric acid, at a pH of 4.

Intermediate Acting Insulin

Intermediate-acting insulin has a longer lifespan than short-acting insulin but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE® insulin. NPH insulin contains protamine which slows down the speed of absorption so that the insulin takes longer to reach the bloodstream but has a longer peak and lifespan. Intermediate acting insulins may be combined with rapid acting insulins at neutral pH, to reduce the total number of injections per day.

Long Acting Insulin

LANTUS® (insulin glargine) is a recombinant human insulin analog that can have up to 24 hour duration. It differs from human insulin by having a glycine instead of asparagine at position 21 and two arginines added to the carboxy-terminus of the beta-chain. LANTUS® consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml). The pH is adjusted with HCl to 4.

The median time between injection and the end of the pharmacological effect for a maximum of 24 hours after the injection. The median time between injection and the end of pharmacological effect was 24 hours for insulin glargine 14.5 hours for NPH human insulin The package insert says not to mix LANTUS® with any other types of insulin, unlike most rapid acting and intermediate acting insulins, due to precipitation of the insulins on mixing.

In the case of insulin glargine, there is no precipitate formed on mixing with VIAJECT™ which also has a pH of 4, matching that of the insulin glargine. Ultimately, this combination provides very rapid acting insulin to carry the patient through a meal with less bolus insulin, since it is very rapidly absorbed and eliminated shortly after meal digestion, thereby reducing the chance of hypoglycemia and providing 24 hour long lasting basal insulin. This ultimately reduces the number of injections required per day from four to three.

B. Acid Stabilizers and Chelators

Acid Stabilizers

Acids which effectively solubilize hexameric crystalline insulin are selected based on their molecular size and pKa, and are predicted to be most effective in masking the charges on the insulin molecule which are exposed upon dissociation into the monomeric or dimeric form FIG. 1. Specific acids preserve bioactivity, effectively charge mask and increase the rate of absorption following dissociation of hexameric insulin into the monomeric form The examples establish the importance of the acid in both in vitro (human oral epithelial cells) and in vivo (rat, pig and human). Regular human insulin (HUMULIN®) is solubilized with HCl, formulated at physiological pH. Pharmacokinetic profiles of this insulin show the insulin is not absorbed very rapidly, having a peak insulin concentration at approximately two hours post dose.

Preferred acids are "polyacidic", i.e., have multiple acidic residues. The preferred polyacids include aspartic, glutamic, succinic, fumaric, maleic and citric acids. The useful concentration range is 0.1 to 3 mg/ml acid, for solutions containing 0.5 to 4 mg insulin/ml. The range of pH is 3.0 to 4.2, while the preferred range is 3.8-4.1. These acids may be used in conjunction with any rapid acting insulin to reduce pH and make them soluble following mixing with LANTUS®.

Chelators

In the preferred embodiment, a chelator is mixed with the active agent. The chelator, in addition to its primary role in chelation, is also believed to hydrogen bond with the insulin, thereby masking the charge and facilitating absorption of the insulin. It is believed that the chelator pulls the zinc away from the insulin, thereby favoring the monomeric form of the insulin over the hexameric form following injection into subcutaneous tissue (e.g. mucosa, or fatty tissue). This facilitates absorption of the insulin by keeping it monomeric. In addition, the chelator further assists in absorption by hiding or charge masking exposed surface charges on the insulin molecule.

The chelator may be ionic or non-ionic. Suitable chelators include ethylenediaminetetraacetic acid (EDTA), citric acid, dimercaprol (BAL), penicillamine, alginic acid, chlorella, cilantro, alpha lipoic acid, dimercaptosuccinic acid (DMSA), dimercaptopropane sulfonate (DMPS), and oxalic acid. In the preferred embodiment, the chelator is EDTA. Ions may be part of the active agent, added to the stabilizing agent, mixed with the chelator, and/or included in the coating. Representative ions include zinc, calcium, iron, manganese, magnesium, aluminum, cobalt, copper, or any di-valent metal or transitional metal ion. $Zn^{+2}$ has a stronger binding preference for EDTA than $Ca^{+2}$.

C. Formulations

The active compounds or pharmaceutically acceptable salts thereof may be administered in the form of a pharmaceutical composition wherein the active compound(s) is in admixture or mixture with one or more pharmaceutically acceptable carriers, excipients or diluents. In a preferred embodiment the insulin is administered by injection. Alternatively, the compositions may be administered by oral, buccal, sublingual, vaginal, rectal, or nasal administration Liquid Formulations Liquid formulations may be injected (s.c., i.m., i.p) or sprayed for nasal, sublingual, vaginal, or buccal administration. The formulation for injection will typically be suspended in sterile water, phosphate buffered saline, saline or glycerin. Other suitable pharmaceutically acceptable agents are known. These will typically be added to the insulin in lyophilized or dried form immediately before use, but may be added prior to use.

Figure 8:
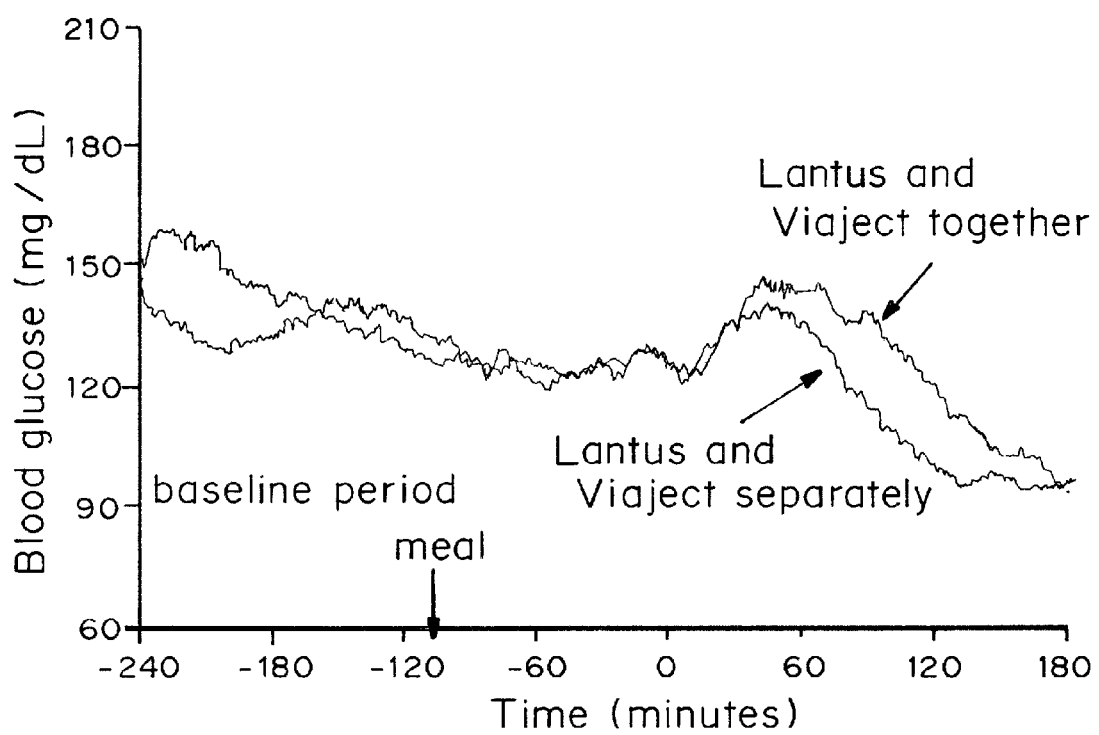
FIG. 8 is a graph of continuous blood glucose values over time (hours) from a human clinical trial, where insulin glargine (LANTUS®) and VIAJECT™ were administered separately (two injections) or together, combined in one injection.

Solubilizing agents include wetting agents such as polysorbates and poloxamers, non-ionic and ionic surfactants, food acids and bases (e.g. sodium bicarbonate), and alcohols, and buffering acids or salts for pH control. FIG. 8 shows data on human clinical trials on the injectable mixture of VIAJECT™ and insulin glargine.

Solid Formulations

Solid or semi-solid gels may be formulated for s.c. injection (syringable low viscosity gels) or dried into a film for buccal, sublingual, oral, rectal, or vaginal administration of the dual acting insulin. They may be formed by mixing one or more hydrophilic polymers in solution, which gel or solidify by ionic and/or covalent binding. Suitable materials include, but are not limited to, starch, pregelatinized starch, gelatin, sugars (including sucrose, glucose, dextrose, lactose and sorbitol), chitosans (various forms) dextrin, maltodextrin, polyethylene glycol, waxes, natural and synthetic gums such as acacia, guar gum, tragacanth, alginate, sodium alginate, celluloses, including hydroxypropylmethylcellulose, carboxymethylcellulose sodium, hydroxypropylcellulose, hydroxylethylcellulose, ethylcellulose, methyl cellulose, and veegum, hydrogenated vegetable oil, Type I, magnesium aluminum silicate, and synthetic polymers such as acrylic acid and methacrylic acid copolymers, carbomer, methacrylic acid copolymers, methyl methacrylate copolymers, aminoalkyl methacrylate copolymers, polyacrylic acid/polymethacrylic acid, and polyvinylpyrrolidone. Blending or copolymerization sufficient to provide a certain amount of hydrophilic character can be useful to improve wettability and mucoadhesion of the materials. For example, about 5% to about 20% of monomers may be hydrophilic monomers. Hydrophilic polymers such as hydroxylpropylcellulose (HPC), hydroxypropylmethylcellulose (HPMC), carboxymethylcellulose (CMC) are commonly used for this purpose. Preferably, the polymers are bioerodible, with preferred molecular weights ranging from 1000 to 15,000 Da, and most preferably 2000 to 5000 Da. These can also be nonionic polymers such as ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

In one embodiment, the formulation is a sublingual solid formulation that contains excipients, such as poly(vinyl alcohol), glycerin, carboxymethyl cellulose (CMC), chitosan and optionally poly(ethylene glycol) and water. The composition may be in the form of a clear or opaque, flexible, thin material. Typical thicknesses range from 0.01 to 4 mm. The film may have any suitable shape, including round, oval, rectangle, or square. The film may be a monolayer, bilayer or trilayer film. In the preferred embodiment, the film is designed to be suitable for sublingual administration. The monolayer film contains an active agent and one or more excipients. The bilayer film contains one or more excipients, such as a solubilizing agent and/or a metal chelator, in a first layer, and an active agent in the second layer. This configuration allows the active agent to be stored separated from the excipients, and may increase the stability of the active agent, and optionally increases the shelf life of the composition compared to if the excipients and active agent were contained in a single layer. The trilayer film contains three layers of film. Each of the layers may be different, or two of the layers, such as the bottom and top layers, may have substantially the same composition. In one embodiment, the bottom and top layers surround a core layer containing the active agent. The bottom and top layers may contain one or more excipients, such as a solubilizing agent and a metal chelator. Preferably the bottom and top layers have the same composition. Alternatively, the bottom and top layers may contain different excipient(s), or different amounts of the same excipient(s). The core layer typically contains the insulin, optionally with one or more excipients. In one embodiment, the film is a bilayer film that contains EDTA and citric acid in one layer and insulin in the second layer. Each layer may contain additional excipients, such as glycerin, polyvinyl alcohol, carboxymethyl cellulose, and optionally PEG (such as PEG 400 or PEG 1600). In one embodiment, a third layer can be located between the insulin layer and the layer containing the other ingredients to further protect the active agent from degradative ingredients located in the other layer during storage. Suitable materials for the protective layer include carboxymethylcellulose sodium, carnauba wax, cellulose acetate phthalate, cetyl alcohol, confectioner's sugar, ethylcellulose, gelatin, hydroxyethyl cellulose, hydroxypropyl methylcellulose, liquid glucose, maltodextrin, methylcellulose, microcrystalline wax, polymethacrylates, polyvinyl alcohol, shellac, sucrose, talc, titanium dioxide, and zein. By altering the composition of the excipients, the film can be designed to dissolve rapidly (less than 30 seconds) or slowly (up to 15 minutes) in order to achieve the desired absorption profile and subsequent effect. The film may dissolve in a time period ranging from 3 to 5 minutes, 5 to 8 minutes, or 8 to 15 minutes. Preferably, the film dissolves in a time period ranging from 2-10 minutes.

There are a number of colorings and flavorings that are commercially available. Flavorings include mint, lemon, cherry, bubblegum, and other standard flavors. Sweeteners can be added, including non-glucose sweeteners, which are particularly advantageous for administration of insulin. Colorings can be red, blue, green, yellow, orange, or any other standard FDC approved color.

Stabilizers are used to inhibit or retard drug decomposition reactions which include, by way of example, oxidative reactions. A number of stabilizers may be used. Suitable stabilizers include polysaccharides, such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphosphatidylserine; phosphatidylglycerols; phosphatidylinositols; cardiolipins; sphingomyelins; and synthetic detergents, such as dioctanoylphosphatidyl choline and polyethylene-polypropylene glycol). Other suitable stabilizers include acacia, albumin, alginic acid, bentonite, carboxymethylcellulose calcium, carboxymethylcellulose sodium, cyclodextrins, glyceryl monostearate, hydroxypropyl cellulose, hydroxypropyl methylcellulose, magnesium aluminum silicate, propylene glycol, propylene glycol alginate, sodium alginate, white wax, xanthan gum, and yellow wax. In the preferred embodiment, the agent is insulin and the stabilizer may be a combination of one or more polysaccharides and glycerol, bacteriostatic agents, isotonic agents, lecithins, or synthetic detergents.

II. Methods of Making the Formulations

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Proper formulation is dependent upon the route of administration chosen.

III. Methods of Using Formulations

The formulations may be administered in a variety of manners, including by injection, preferably subcutaneously, or topically to a mucosal surface such as oral, buccal, nasal, sublingual, rectal, vaginal, pulmonary, or ocular administration. Subcutaneous, buccal or sublingual are preferred. Following administration, the dosage form dissolves quickly releasing the drug or forming small particles containing drug, optionally containing one or more excipients. The formulation is designed to be rapidly absorbed and transported to the plasma for systemic delivery.

In the preferred embodiment, the formulation is formed by mixing a powdered active agent with a liquid diluent that contains a pharmaceutically acceptable liquid carrier and one or more solubilizing agents. In the most preferred embodiment, the active agent is insulin, and the diluent contains saline or glycerin, EDTA and citric acid. Prior to administration the powder and diluent are mixed together to form an injectable composition.

The present invention will be further understood by reference to the following non-limiting examples.

Example 1

Effect of EDTA on Insulin Absorption Through an Epithelial Cell Multilayer

Purpose: To demonstrate in vitro the effect of EDTA in the presence of citric acid on absorption of insulin through an epithelial cell multilayer.

Figure 2:
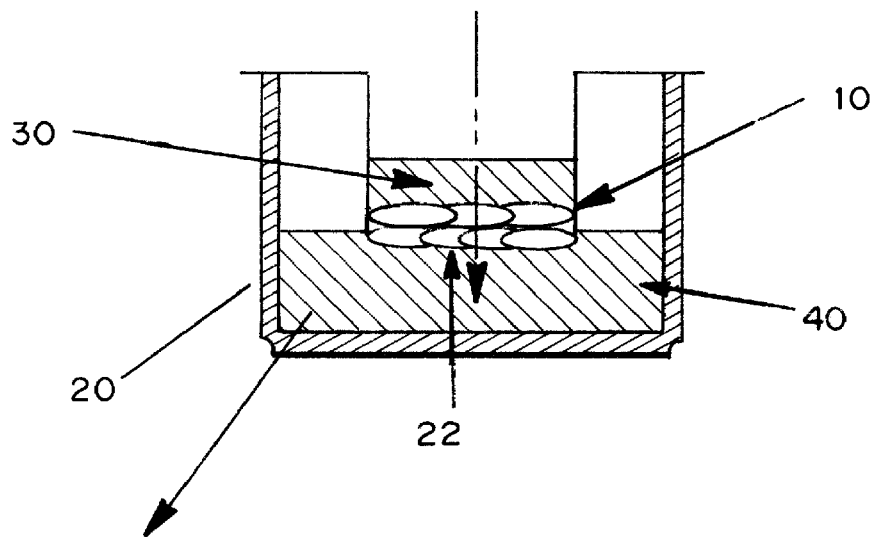
FIG. 2 is a diagram of the transwell device used to measure insulin absorption through oral epithelial cells.

Materials and Methods:

Two saline solutions were mixed. The first contained 1 mg/ml insulin 2 mg/ml EDTA and 2 mg/ml citric acid ("solution 1"). The second contained 1 mg/ml insulin and 2 mg/ml citric acid ("solution 2"). The control (no cells) contained EDTA, citric acid and insulin. Immortalized human epithelial cell line cultures (10) were seeded on transwell plates (20) FIG. 2. Cells were grown to confluence and tested for membrane integrity using trans-epithelial resistance. A 0.1 μm filter (22) was used. At time zero, the fluid in the top chambers, i.e., donor chamber (30), of the transwell plates was replaced with 0.5 ml of insulin solution, either solution 1 or solution 2. Two plates with solution 1, two plates with solution 2 and one plate with the control solution (no cells) were tested simultaneously. The lower chamber, i.e., receiver chamber (40) of each plate contained 1.5 mL of saline solution. At each time point, 100 μL of fluid from the lower chamber (40) was removed and analyzed with insulin Enzyme-Linked Immunosorbent Assay (ELISA). 100 μl of saline was added to the lower chamber to maintain a constant volume of 1.5 mL throughout the study.

Figure 3:
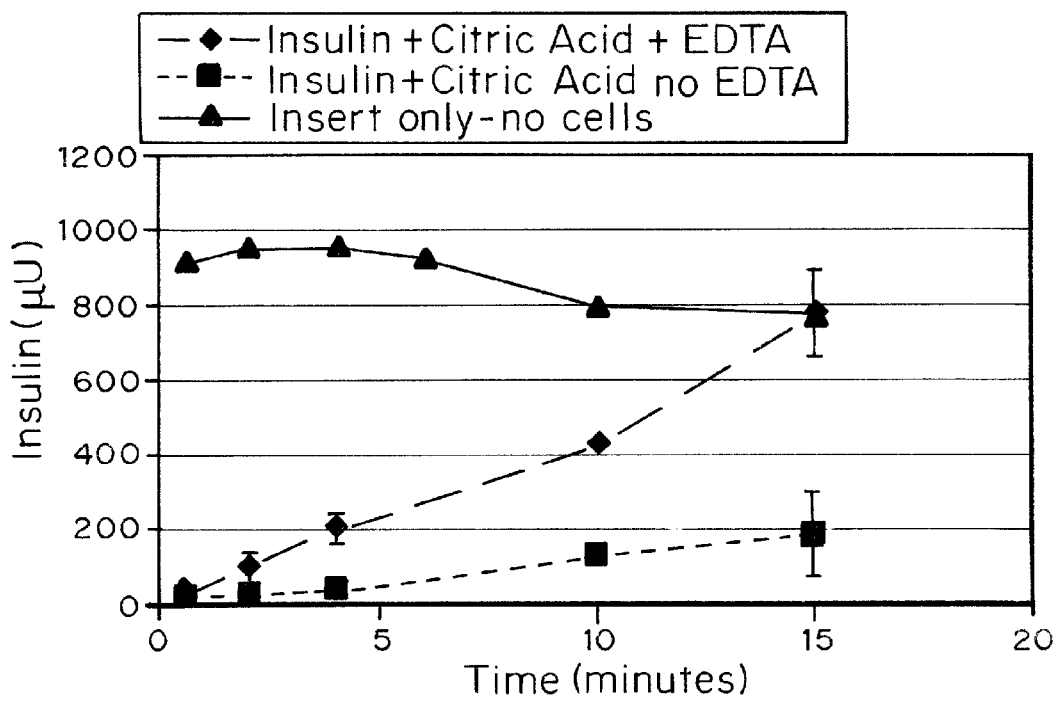
FIG. 3 is a graph of the mean insulin accumulation (μU) over time (minutes) in the lower chamber of a transwell membrane plate seeded with epithelial cells, comparing the effect of an insulin formulation containing EDTA (♦) with one without EDTA (■), with a control, no cells (▲).

Results:

FIG. 3 is a graph of the mean insulin accumulation (μU) over time (minutes) in the lower chamber of a transwell plate seeded with epithelial cells, comparing the effect of an insulin formulation containing EDTA (♦) with one without EDTA (■), with a control, no cells (▲).

Solution 1, which contained EDTA, moved through the multilayer of epithelial cells more effectively than solution 2, which did not contain EDTA. Therefore, the effect of combining EDTA with citric acid is to promote the speed and amount of absorption.

Example 2

Effect of Aspartic and Citric Acid on Absorption of Insulin Through an Epithelial Cell Multilayer Purpose: Demonstrate that polyacids have different affinities for insulin with EDTA as shown by an increase in absorption through cells.

Figure 4:
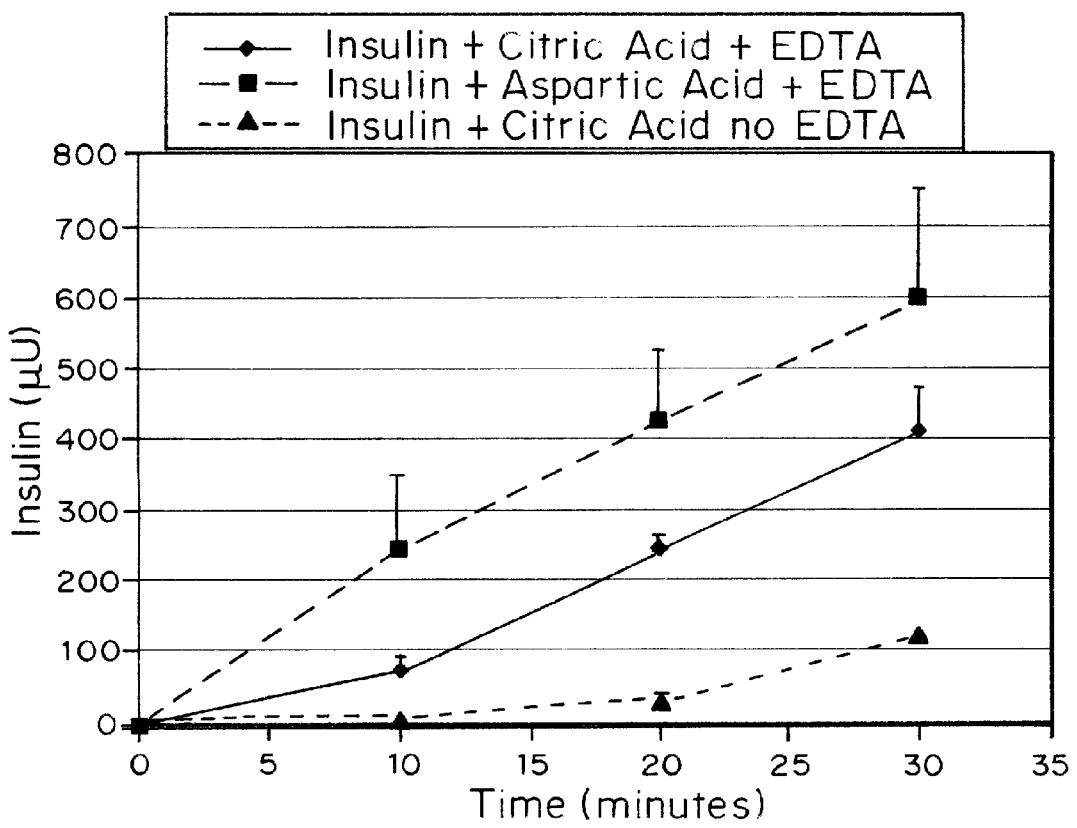
FIG. 4 is a graph of cumulative insulin (U) over time in minutes for samples of citric acid with and without EDTA versus aspartic acid with EDTA.

Methods and Materials:

Oral epithelial cells that have been seeded on transwell plates were used to determine the rate of absorption through the cell multilayer, as described in example 1. Insulin (1 mg/ml) was dissolved in either aspartic (0.2 mg/mL) or citric acid (2 mg/ml) and EDTA (2 mg/ml) was added to both. Insulin with citric acid (no EDTA) was used as a control. The pH of the solution was approximately 3.5 to 4, and physiological saline was present to provide an isotonic environment for the cells (0.85% NaCl, sufficient to produce a range of 280-310 mOsm as measured by freezing point depression, Microsmette, Precision systems, Natick, Mass.). Samples were taken from the receiver chamber and assayed by ELISA (Linco Corp.) for human recombinant insulin (µU/mL). Results: Insulin/citric acid absorption through the cell layers was enhanced by the addition of EDTA (as seen in example 2). However, aspartic acid was even more potent at enhancing insulin transport in the presence of EDTA FIG. 4. Conclusion: Different polyacids in the presence of EDTA have varying effects on insulin absorption, possibly due to varying degrees of charge masking.

Example 3

Comparison of Effect of Citric Acid, Glutamic Acid, Adipic Acid and Oxalic Acid on Insulin Absorption Through an Epithelial Cell Multilayer Materials and Methods:
Transwell plates seeded with oral epithelial cells were used for these experiments. The effect of EDTA was monitored by the amount of insulin that came through the lower chamber of the transwell plate.
Oral epithelial cells were grown on transwell inserts for 2 weeks until multiple (4-5) cell layers had formed. Transport studies were conducted by adding the appropriate solution (all contained 1 mg/ml human insulin) to the donor well and removing samples from the receiver well after 10 minutes. Insulin amounts in the receiver wells were assayed using ELISA. Apparent Permeability was calculated using the formula: Apparent Permeability=Q/A(C)t where Q=total amount permeated during incubation time in µg, A=area of insert in $cm^2$, C=initial concentration in donor well in $\mu g/cm^3$ and t=total time of experiment in sec.
EDTA concentration is 0.45 mg/mL in all cases and the acid concentrations are as follows: Citric acid 0.57 mg/ml, Glutamic acid 0.74 mg/mL, Adipic acid 0.47 mg/mL, Oxalic acid 0.32 mg/mL. The pH of the solutions was 3.6 in all cases.

Figure 5:
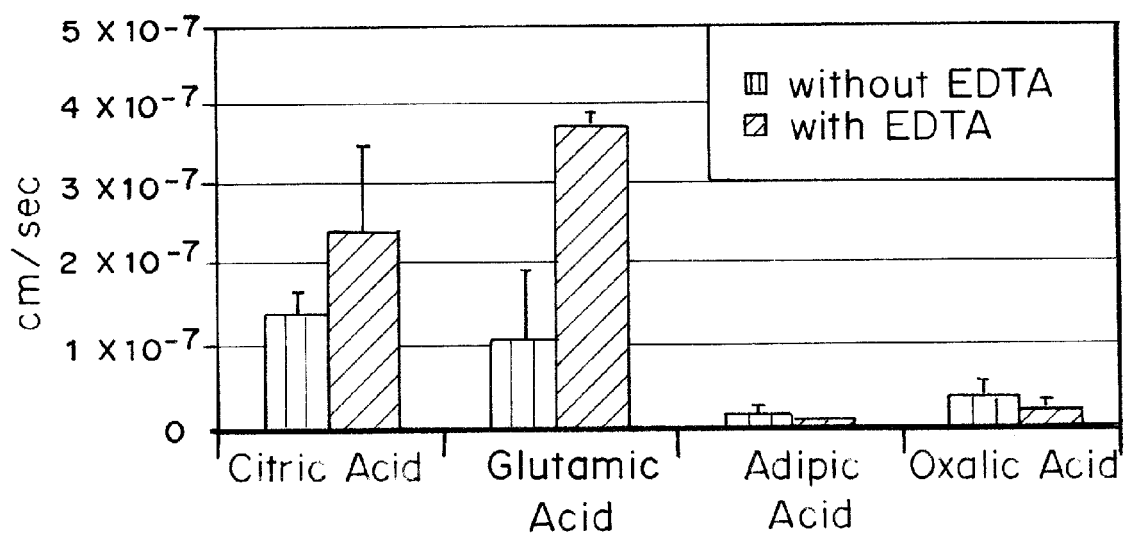
FIG. 5 is a graph of insulin apparent permeability for insulin with (diagonal lines) and without (vertical lines) EDTA, for samples with citric acid, glutamic, adipic, and oxalic acid, over time in minutes.

Results:
FIG. 5 shows the change in apparent permeability resulting from different organic polyacids that have been tested, with and without EDTA. The results show that there is an increase in the cumulative amount of insulin apparent permeability when EDTA is added to the acid/insulin in the case of citric and glutamic acids. This did not hold true for all organic polyacids. Adipic and oxalic acids did not show such a response.

Example 4

Effect of Acid on Absorption of Insulin from Polymeric Gel Administered Rectally to Rats Purpose: To observe effect of acids and EDTA in an in vivo model.
Materials and Methods:
Samples
Insulin was incorporated into a gel consisting of PVA (0.5%), Carbopol (2.7%), CMC (0.005%) and PEG 400 (0.14%), glycerin (0.14%), and EDTA (0.005%) by blending with insulin/aspartic acid or insulin/HCl. The final concentration of insulin in insulin/aspartic acid gel was 0.7 and insulin concentration in insulin/HCl gel was 1.7 mg/g.

Rat Rectal Study:
Rats were fasted overnight and were cleared of all fecal matter with a warm water enema. Then the gel formulation was inserted into the rectum and the rat's blood glucose was monitored over an 8 hour time period.

Figure 6:
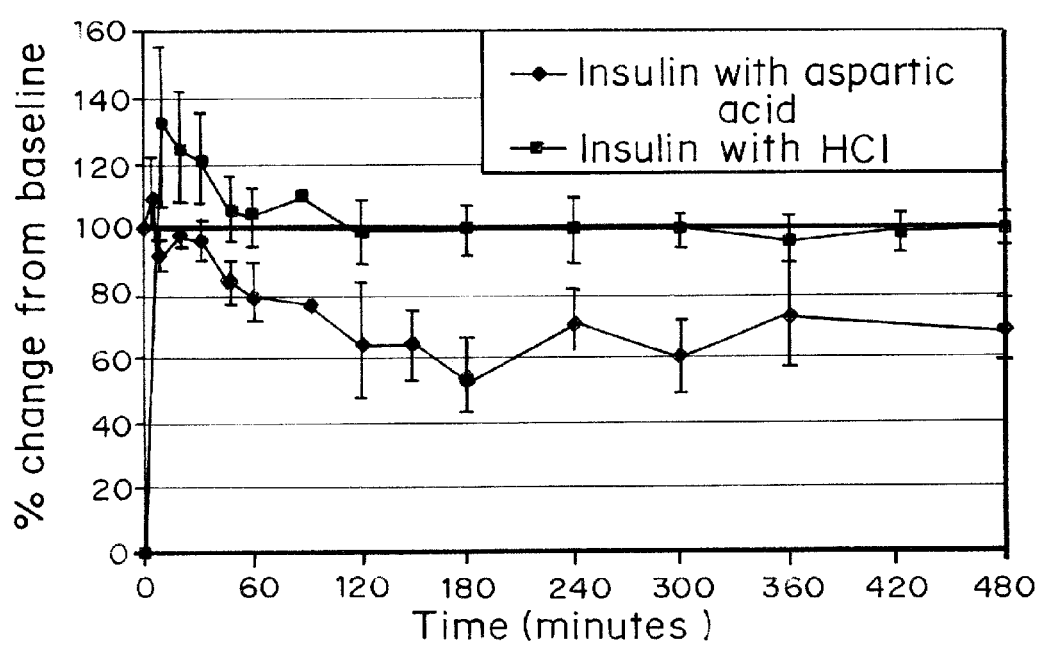
FIG. 6 is a graph of percent glucose lowering from baseline over time in minutes comparing insulin with aspartic acid and EDTA with insulin with HCl and EDTA in rats.

Results:
The results are shown in FIG. 6 as a percent glucose lowering from baseline comparing insulin with aspartic acid and EDTA to insulin with HCl and EDTA. The results show significantly better lowering of glucose for the insulin containing aspartic acid as compared to insulin containing HCl.

Example 5

Comparison of Effect of HCl and Citric Acid on Absorption of Insulin with EDTA in Miniature Diabetic Swine Purpose: To look at timing of glucose response when insulin is injected with a polyacid or organic acid in conjunction with EDTA.

Materials and Methods
To further demonstrate that the type of acid is important to the rapid action of the dissociated insulin, a comparison of citric acid to HCl, was performed in miniature diabetic swine. Insulin (0.9 mg/mL) was prepared as a clear isotonic solution containing citric acid (1.8 mg/mL), EDTA (1.8 mg/mL), and m-cresol as a preservative, pH ~4. The comparator was prepared in the same manner, substituting HCl (0.001N) for citric acid and adjusting the pH with NaOH to approximately 4,
Diabetic mini pigs were not fed on the day of the study and were dosed with 0.08 U/kg on three occasions with the HCl formulation. For comparison, the citric acid formulation was used on two occasions with this dose, and four other occasions at a higher dose of 0.125 U/kg. Blood was drawn for insulin and glucose determination over the 8 hour study period.

Figure 7:
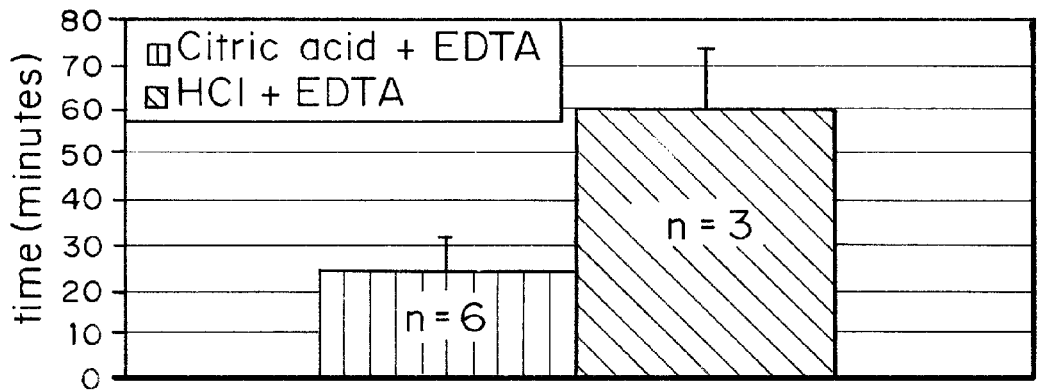
FIG. 7 is a graph of mean glucose levels in miniature swine over time, comparing insulin with EDTA and citric acid versus insulin with EDTA and HCl.

Results:
The results shown in FIG. 7 compare the time to reach the lowest glucose level (nadir) following insulin administration to diabetic mini-pigs. The citric acid formulation was consistently faster at reaching the nadir than an identical formulation made with HCl.

Example 6

Insulin Glargine and VIAJECT™ Administered Together and Separately to Patients with Diabetes Methods and Materials:
Blood glucose ("BG") of 9 patients (5 males and 4 females; age 40±10 yrs, body mass index ("BMI") 24.0±2.0 $kg/m^2$) were stabilized by glucose clamps (target BG 120 mg/dl). Prior to dosing, the glucose infusion was turned off. Using a cross over design with random treatment order, the same patient specific dose of VIAJECT™ and Lantus LANTUS® was injected s.c. immediately before the meal. On one occasion, the doses were together in the same injection. On another occasion the identical dose of each insulin was administered separately in two injections. Blood glucose was continuously monitored for 8 hours and glucose infusion was re-initiated if BG was less than 60 mg/dl. Plasma insulin levels were determined throughout the study.

Results:

The mean blood glucose data over the first three hours is shown in FIG. 8. The first three hours have a very similar profile, which is typical to the rapid action of VIAJECT™ after a meal.

Modifications and variations of the formulations and methods of use will be obvious to those skilled in the art from the foregoing detailed description and are intended to come within the scope of the appended claims.

We claim:

1. A composition comprising a fast, rapid or very rapid insulin in combination with a long acting insulin, wherein the pH of the composition is adjusted to a pH between 3.0 and 4.2 to solubilize the long acting insulin.

2. The composition of claim 1, wherein the long acting insulin is glargine insulin.

3. The composition of claim 1, comprising rapid acting insulin.

4. The composition of claim 1, further comprising intermediate acting insulin.

5. The composition of claim 1, further comprising a zinc chelator.

6. The composition of claim 5, wherein the chelator is ethylenediaminetetraacetic acid (EDTA).

7. The composition of claim 1, comprising an acid selected from the group consisting of aspartic acid, glutamic acid, maleic, fumaric, succinic and citric acid.

8. The composition of claim 1, further comprising a chelator, and, an acid selected from the group consisting of aspartic, glutamic, succinic, maleic, fumaric and citric acid.

9. The formulation of claim 8 wherein the chelator is EDTA.

10. The formulation of claim 9 wherein the acid is citric acid.

11. The formulation of claim 10 comprising a rapid acting insulin wherein the ratio of insulin:chelator:acid is 1:2:2 (mg/ml).

12. The formulation of claim 1 wherein the insulin is native human insulin, recombinant human insulin, porcine insulin, bovine insulin a derivative of human insulin, or an analog of human insulin suitable for administration to a human.

13. A method of treating a patient with insulin comprising administering to an individual the composition of any of claims 1 or 8.

14. The method of claim 13 wherein the insulin is administered by injection.

15. The method of claim 13 wherein the insulin is in a formulation for administration sublingually, oral, basal, buccal, rectal or vaginally.

* * * * *

UNITED STATES PATENT AND TRADEMARK OFFICE
CERTIFICATE OF CORRECTION

PATENT NO. : 7,718,609 B2
APPLICATION NO. : 11/734161
DATED : May 18, 2010
INVENTOR(S) : Solomon S. Steiner et al.

Page 1 of 1

It is certified that error appears in the above-identified patent and that said Letters Patent is hereby corrected as shown below:

Claim 12, column 12, line 17, replace "bovine insulin" with --bovine insulin,--.

Signed and Sealed this
Sixteenth Day of August, 2011

David J. Kappos
*Director of the United States Patent and Trademark Office*